US012656311B2

(12) United States Patent　　　(10) Patent No.: US 12,656,311 B2
Thrush et al.　　　　　　　　　　　(45) Date of Patent: Jun. 16, 2026

(54) ELECTROPHORESIS APPARATUS WITH MINIMAL AUTOFLUORESCENCE TO ENABLE GEL PROCESSING IN SITU

(71) Applicant: Bio-Rad Laboratories, Inc., Hercules, CA (US)

(72) Inventors: Evan Thrush, San Anselmo, CA (US); Stephen L. Swihart, Walnut Creek, CA (US); Kevin Alan Mcdonald, Novato, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 237 days.

(21) Appl. No.: 17/386,246

(22) Filed: Jul. 27, 2021

(65) Prior Publication Data

US 2022/0026390 A1　　　Jan. 27, 2022

Related U.S. Application Data

(60) Provisional application No. 63/057,248, filed on Jul. 27, 2020.

(51) Int. Cl.
G01N 27/447　　　(2006.01)
G01N 21/64　　　(2006.01)
G01N 33/68　　　(2006.01)

(52) U.S. Cl.
CPC ... G01N 27/44726 (2013.01); G01N 21/6428 (2013.01); G01N 27/44782 (2013.01); G01N 33/6803 (2013.01)

(58) Field of Classification Search
CPC ....... G01N 27/44726; G01N 27/44782; G01N 27/44721; G01N 21/6428; G01N 21/6456; G01N 33/6803; G01N 2021/6482
See application file for complete search history.

(56) References Cited

U.S. PATENT DOCUMENTS 6,027,628 A　　2/2000　Yamamura et al.
7,923,054 B2　4/2011　Dutta et al.
(Continued)

FOREIGN PATENT DOCUMENTS

JP　　　4424938 B2　　3/2010
KR　　20050006861 A　　1/2005
(Continued)

OTHER PUBLICATIONS

Piruska et al., The autofluorescence of plastic materials and chips measured under laser irradiation, Lab on a chip, 2005, 5, 1348-1354 (Year: 2005).*

(Continued)

*Primary Examiner* — Shizhi Qian
(74) *Attorney, Agent, or Firm* — Kolisch Hartwell, P.C.

(57)　　　ABSTRACT

An electrophoresis apparatus with minimal autofluorescence to enable gel processing in situ, and methods of making and using the electrophoresis apparatus. An exemplary electrophoresis apparatus may comprise a cassette defining a cavity between a first pane and a second pane of a double-paned viewing window, and also may comprise a slab gel located in the cavity. The viewing window may be transparent to ultraviolet light that drives a derivatization reaction in the slab gel, and, absent the slab gel, may define a window autofluorescence inducible by irradiation with the ultraviolet light. The window autofluorescence, per unit area, may be less than five-fold a gel autofluorescence of the slab gel, per the same unit area and under the same irradiation with the ultraviolet light.

10 Claims, 8 Drawing Sheets

(56) References Cited

U.S. PATENT DOCUMENTS

| | | | |
|---|---|---|---|
| 7,966,060 B2 | 6/2011 | Smit et al. | |
| 8,007,646 B2 | 8/2011 | Edwards et al. | |
| 8,609,423 B2 | 12/2013 | Diller et al. | |
| 9,005,418 B2 | 4/2015 | Belisle | |
| 2002/0096431 A1* | 7/2002 | Sevigny | G01N 27/44782 |
| | | | 204/620 |
| 2006/0024831 A1* | 2/2006 | Kao | B01L 3/50853 |
| | | | 356/243.1 |
| 2006/0068206 A1* | 3/2006 | Hala | B29C 45/16 |
| | | | 264/328.8 |
| 2008/0128281 A1 | 6/2008 | Blikstad et al. | |
| 2009/0127115 A1 | 5/2009 | Bielawski | |
| 2009/0314641 A1* | 12/2009 | Rooney | G01N 33/561 |
| | | | 204/546 |
| 2010/0213065 A1 | 8/2010 | Astrom et al. | |
| 2013/0032483 A1 | 2/2013 | Tan et al. | |
| 2015/0153306 A1* | 6/2015 | Strong | G01N 27/44704 |
| | | | 204/620 |
| 2018/0252676 A1* | 9/2018 | McKee | G01N 27/44704 |

FOREIGN PATENT DOCUMENTS

| | | | | |
|---|---|---|---|---|
| WO | WO-2015079048 A1 * | 6/2015 | | C12Q 1/37 |
| WO | 2017053531 A1 | 3/2017 | | |

OTHER PUBLICATIONS

Piruska, Aigars et al. , "The autofluorescence of plastic materials and chips measured under laser irradiation", Lab on a Chip, vol. 5, Nov. 1, 2005, pp. 1348-1354.

Rodriguez, Kari, Authorized Officer, Commissioner for Patents, U.S. Patent and Trademark Office, "International Search Report" in connection with related International Application No. PCT/US2021/ 043328, Dec. 29, 2021, 9 pgs.

Rodriguez, Kari, Authorized Officer, Commissioner for Patents, U.S. Patent and Trademark Office, "Written Opinion of the International Searching Authority" in connection with related International Application No. PCT/US2021/ 043328, Dec. 29, 2021, 8 pgs.

European Patent Office, "Extended European Search Report" in connection with related European Patent Application No. 21849383. 1, dated Jul. 19, 2024, 11 pgs.

China National Intellectual Property Administration, First Office Action regarding Chinese Patent Application No. 202180062726.6, dated Oct. 22, 2025, 19 pages.

* cited by examiner

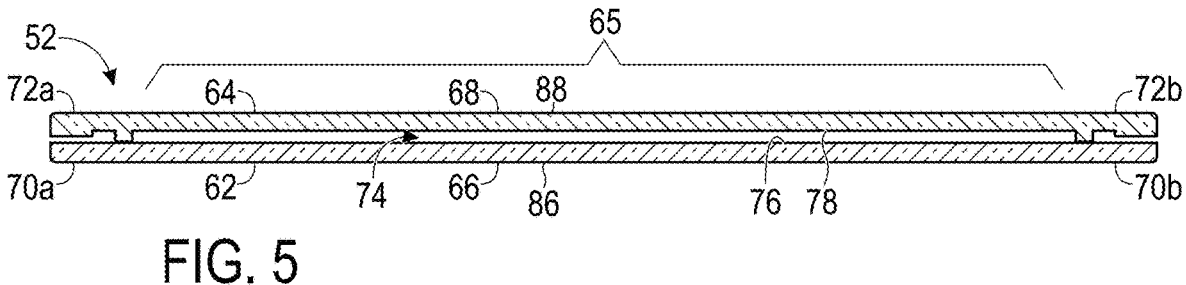
FIG. 5
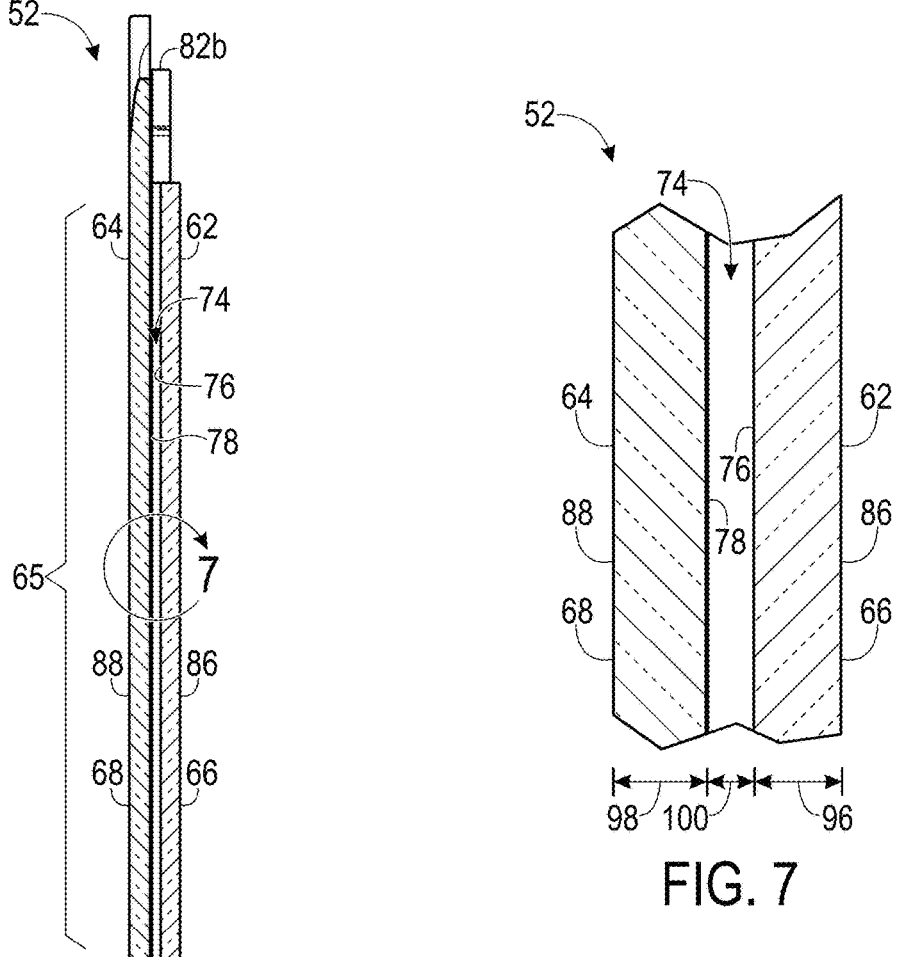
FIG. 6
FIG. 7

110

112

LOAD A SAMPLE(S) INTO A WELL(S) OF A GEL HELD IN A CASSETTE

114

DRIVE A SAMPLE COMPONENT(S) IN THE GEL BY ELECTROPHORESIS

116

DERIVATIZE THE SAMPLE COMPONENT(S) UNDER UV IRRADIATION TO ALTER THEIR FLUORESCENCE WHILE THE GEL REMAINS IN THE CASSETTE

118

INDUCE FLUORESCENCE IN THE GEL WHILE THE GEL REMAINS IN THE CASSETTE

120

DETECT THE FLUORESCENCE

130

132
INJECTION MOLD PARTS EACH DEFINING A SITE OF POLYMER INJECTION

134
ATTACH AT LEAST A PORTION OF EACH OF THE PARTS TO ONE
ANOTHER TO CREATE A CASSETTE HAVING A VIEWING WINDOW
THAT AVOIDS EACH SITE OF POLYMER INJECTION

136
FORM A SLAB GEL IN A CAVITY OF THE CASSETTE

| | NAME | AUTOFLUORESCENCE |
|---|---|---|
| A | LUCITE UTRAN | 630 |
| B | CA-41 UVT-LL2 | 1500 |
| C | CA-83 UVT | 2740 |
| D | CA-83 UVT (A) | 2120 |
| E | CA-2X | 10600 |
| F | CA-83 UVT (N) | 48000 |
| G | CA-41 UVT | 3460 |

ELECTROPHORESIS APPARATUS WITH MINIMAL AUTOFLUORESCENCE TO ENABLE GEL PROCESSING IN SITU

CROSS-REFERENCE TO PRIORITY APPLICATION

This application is based upon and claims the benefit under 35 U.S.C. § 119(e) of U.S. Provisional Patent Application Ser. No. 63/057,248, filed Jul. 27, 2020, which is incorporated herein by reference in its entirety for all purposes.

INTRODUCTION

Polyacrylamide gel electrophoresis (PAGE) is a widely used laboratory technique for resolving proteins of a sample according to molecular weight. In traditional PAGE, a polyacrylamide gel is formed by polymerization of acrylamide between a pair of plates separated by lateral spacers, and in the presence of a comb to form wells. The gel typically contains a denaturing agent, sodium dodecyl sulfate (SDS), to denature proteins and give each protein a charge proportional to its molecular weight. Protein-containing samples are loaded into the wells, and then driven along respective lanes of the gel from the wells by application of an electrical potential. Proteins within a given lane travel at different velocities according to protein size, which separates proteins of different molecular weight from one another. After electrophoresis is complete, one or both of the plates are removed, which allows the gel (or proteins therein) to be processed further, such as stained with a visible stain for the presence of protein and then imaged, among others.

A procedure for "stain-free" fluorescence detection of proteins has been developed. In the procedure, a modifying agent is incorporated into the gel prior to or during electrophoresis. The modifying agent is not fluorescent and thus can be distributed uniformly throughout the gel without substantially increasing background. However, irradiation of the gel with ultraviolet light after electrophoresis encourages the modifying agent to react locally within the gel with tryptophan residues of proteins. The reaction forms derivatized proteins containing modified tryptophan residues that emit light with a peak in the visible spectrum when excited with ultraviolet light. The visible light emitted by the derivatized proteins is detectable to produce a fluorescence image of the gel. To prevent the plates from interfering with the labeling and imaging steps, at least one of the plates is typically removed prior to performing these steps.

SUMMARY

The present disclosure provides an electrophoresis apparatus with minimal autofluorescence to enable gel processing in situ, and methods of making and using the electrophoresis apparatus. An exemplary electrophoresis apparatus may comprise a cassette defining a cavity between a first pane and a second pane of a double-paned viewing window, and also may comprise a slab gel located in the cavity. The viewing window may be transparent to ultraviolet light that drives a protein-derivatizing reaction in the slab gel, and, absent the slab gel, may define a window autofluorescence inducible by irradiation with the ultraviolet light. The window autofluorescence, per unit area, may be less than five-fold a gel autofluorescence of the slab gel, per the same unit area and under the same irradiation with the ultraviolet light.

BRIEF DESCRIPTION OF THE DRAWINGS

FIG. 5 is a horizontal sectional view of the electrophoresis apparatus of FIG. 1, taken generally along line 5-5 of FIG. 3 in the absence of the slab gel.

FIG. 6 is a vertical sectional view of the electrophoresis apparatus of FIG. 1, taken generally along line 6-6 of FIG. 3 in the absence of the slab gel.

FIG. 7 is a fragmentary sectional view of the electrophoresis apparatus of FIG. 1, taken generally around the region indicated at "7" in FIG. 6.

DETAILED DESCRIPTION

The present disclosure provides an electrophoresis apparatus with minimal autofluorescence to enable gel processing in situ, and methods of making and using the electrophoresis apparatus. An exemplary electrophoresis apparatus may comprise a cassette defining a cavity between a first pane and a second pane of a double-paned viewing window, and also may comprise a slab gel located in the cavity. The viewing window may be transparent to ultraviolet light that drives a protein-derivatizing reaction in the slab gel, and, absent the slab gel, may define a window autofluorescence inducible by irradiation with the ultraviolet light. The window autofluorescence, per unit area, may be less than five-fold a gel autofluorescence of the slab gel, per the same unit area and under the same irradiation with the ultraviolet light.

The inventors have found that forming the plates of an electrophoresis apparatus with a UV transparent polymer is not sufficient for successful stain-free fluorescence imaging in situ (i.e., without removing at least one plate). The sensitivity of detection is low; even abundant proteins often are undetectable. However, if the UV transparent polymer also has minimal autofluorescence, the sensitivity of detection is much higher, such that proteins of higher and lower abundance can be detected.

The inventors also have found that the site of polymer injection for an injection-molded part of an electrophoresis apparatus can generate increased autofluorescence that interferes with detection of fluorescent protein derivatives. The present disclosure provides an improved electrophoresis apparatus having a cassette in which the site of polymer injection of each molded part avoids the viewing window, which reduces or eliminates interference between each site of polymer injection and a resolving portion of the gel. The site of polymer injection defined by each molded part may be present in the cassette at a location offset from the viewing window, or may be physically removed (e.g., cut or broken off) such that the site of polymer injection defined by the molded part is not present in the cassette.

Further aspects of the present disclosure are described in the following sections: (I) electrophoresis apparatuses, (II) methods of sample analysis, (III) methods of making an electrophoresis apparatus, (IV) examples, and (V-VI) selected aspects.

I. ELECTROPHORESIS APPARATUSES

This section provides an overview of exemplary electrophoresis apparatuses having minimal UV-inducible autofluorescence; see FIGS. 1-7.

Figure 1:
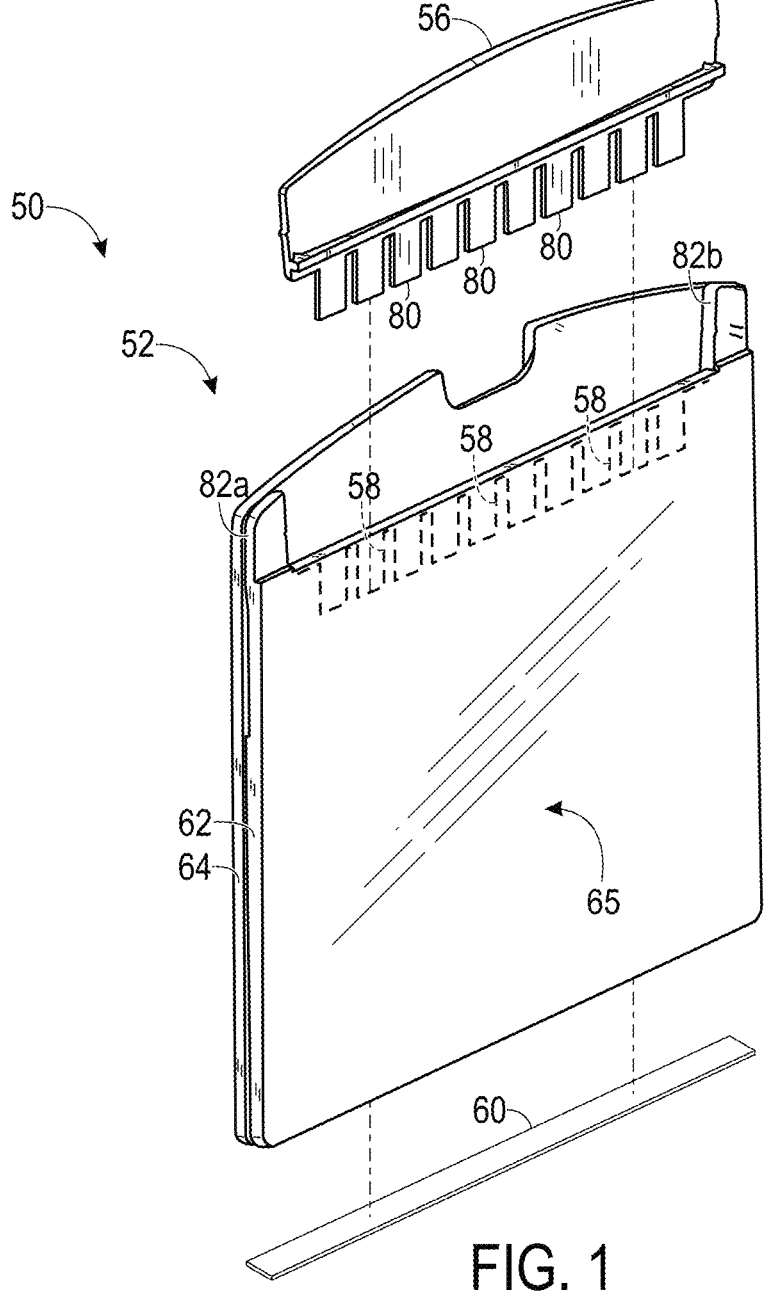
FIG. 1 is a view of an exemplary electrophoresis apparatus including a cassette defining a planar cavity and a double-paned viewing window, a polyacrylamide slab gel located in the planar cavity between panes of the viewing window, a comb that has created wells at a top end of the slab gel, and a sealing member to prevent leakage from the cassette during gel formation, wherein the viewing window is transparent to ultraviolet light (UV) and has minimal UV-induced autofluorescence, thereby permitting UV irradiation of the slab gel and detection of UV-induced fluorescence from fluorescent substances in the gel, while the slab gel remains in the planar cavity of the cassette.
Figure 2:
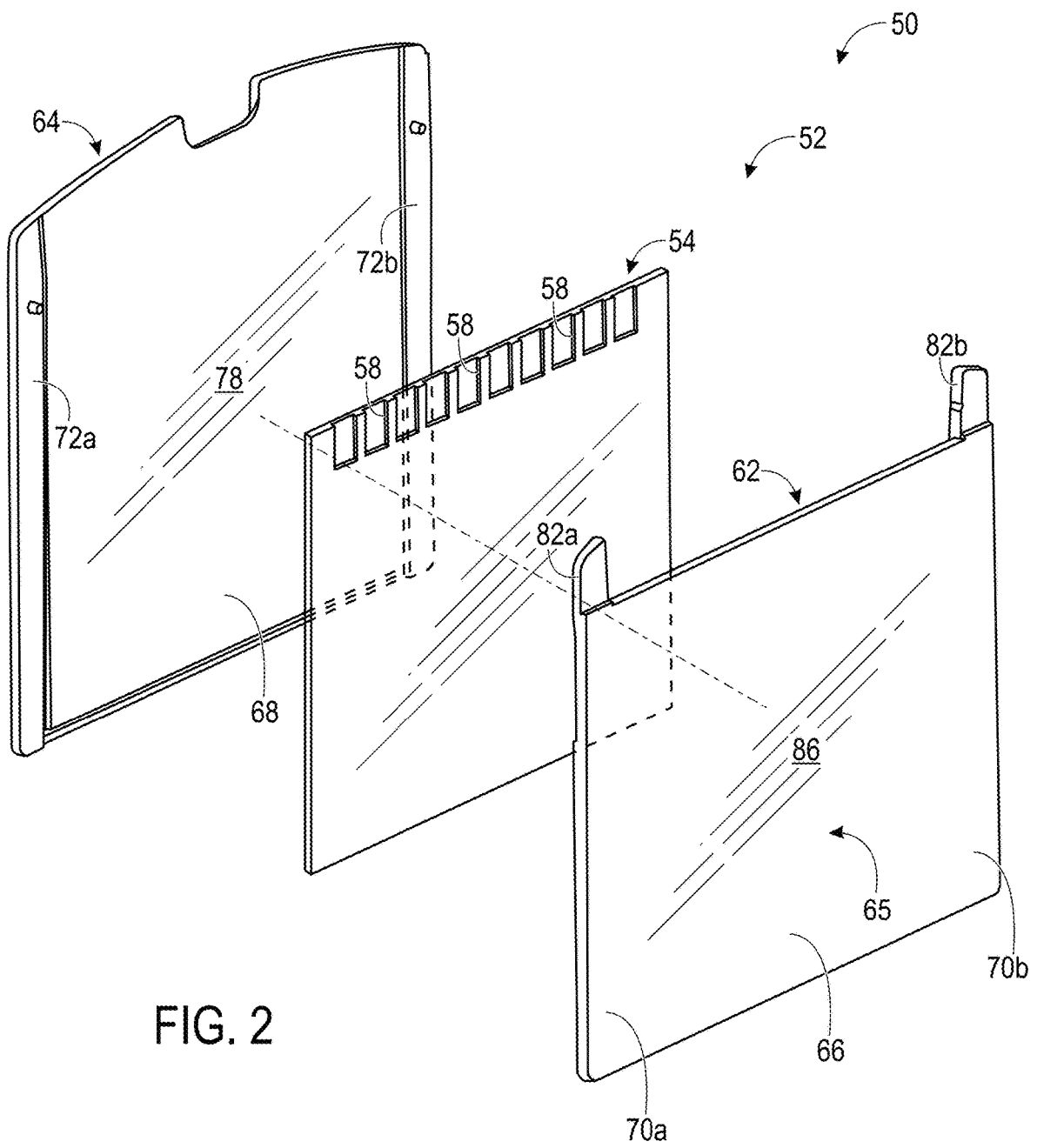
FIG. 2 is an exploded view of the electrophoresis apparatus of FIG. 1 taken in the absence of the comb and the sealing member.

FIGS. 1 and 2 show an exemplary apparatus 50 (an "electrophoresis apparatus") for analyzing samples by gel electrophoresis, to resolve sample components from one another according to size and/or electrical charge. Apparatus 50 may include a cassette 52 (interchangeably called a "container" or "receptacle"). A slab gel 54, optionally having a gel matrix formed of polyacrylamide, may be formed in and held by cassette 52. A comb 56 may be used to create wells 58 along a top edge of slab gel 54 when the slab gel is formed in cassette 52, and then comb 56 may be removed to permit loading of samples into wells 58. A sealing member 60, such as a strip of tape, may seal a bottom edge of cassette 52 during gel formation, to prevent leakage of fluid, and then may be removed (e.g., by a user) before performing gel electrophoresis. Exemplary sample components that may be separated from one another by electrophoresis include proteins, peptides, nucleic acids, and the like.

Cassette 52 may have a front plate 62 and a back plate 64 that face, and are attached to, one another. Plates 62, 64 form a viewing window 65 including a front pane 66 and a back pane 68 each located between a pair of lateral edge portions 70a, 70b or 72a, 72b (see FIGS. 2 and 5-7). Front plate 62 and back plate 64 may be bonded, or otherwise attached, to one another at lateral edge portions 70a and 72a, and at lateral edge portions 70b and 72b, to produce a fluid-tight seal along each lateral edge of a cavity 74 defined by cassette 52 between front pane 66 and back pane 68 (see FIGS. 5-7). In the depicted embodiment, cassette 52 has only two discrete pieces (i.e., front and back plates 62, 64), but in other embodiments, one or more additional pieces may be included, such as discrete lateral spacer elements that separate the plates from one another along their lateral edges.

Cavity 74 is configured to hold slab gel 54. Cavity 74 may be a planar cavity having a pair of planar walls 76, 78 that face one another, where planar walls 76, 78 are provided by respective inner surfaces of front pane 66 and back pane 68. Cavity 74 may have a uniform depth measured between planar walls 76, 78. The lateral edges of cavity 74 may be formed by one or both corresponding lateral edge portions 70a, 72a and one or both corresponding lateral edge portions 70b, 72b along each lateral edge region of cassette 52. The bottom edge of cavity 74 may be sealed by sealing member 60 when slab gel 54 is formed and then opened before electrophoresis by removing the sealing member (also see FIG. 1). The top edge of cavity 74 may receive teeth 80 of comb 56 before slab gel 54 is formed, and then comb 56 may be removed before wells 58 of the slab gel 54 are loaded with samples (e.g., see FIGS. 1 and 2).

Front plate 62 may have a pair of ears 82a, 82b projecting upward from respective lateral edge portions 70a, 70b (see FIGS. 1 and 2). Ears 82a, 82b cooperate with front pane 66 of front plate 62 to form a barrier for retaining running buffer during gel electrophoresis performed with electrophoresis apparatus 50.

Viewing window 65 extends through cassette 52 from an outer surface 86 of front pane 66 to an outer surface 88 of back pane 68 (see FIGS. 2 and 5-7). The width of viewing window 65 may correspond to the width of cavity 74 between lateral edge portions 70a and 70b and/or between lateral edge portions 72a and 72b.

Viewing window 65 is configured to permit slab gel 54 to be irradiated with ultraviolet light in situ, that is, while the gel remains in cavity 74 between front pane 66 and back pane 68. Accordingly, viewing window 65 is transparent to ultraviolet light, such as ultraviolet light of 320-400 nm (UV-A), 280-320 nm (UV-B), and/or <280 nm (UV-C), among others. A viewing window that is "transparent to ultraviolet light" means that a majority of ultraviolet light of a specified wavelength range incident on the viewing window is transmitted through the viewing window and/or to a slab gel located in the cavity between front pane 66 and back pane 68. The majority of ultraviolet light that is transmitted may, for example, be at least 70%, 80%, 85%, or 90%, among others, of the ultraviolet light.

Viewing window 65 also is configured to minimize UV-induced autofluorescence. The viewing window, absent slab gel 54, defines a window autofluorescence inducible by irradiation with ultraviolet light of a given wavelength. To minimize interference from UV-induced autofluorescence, and to permit in situ derivatization of proteins to enhance their fluorescence, and imaging of slab gel 54, the window autofluorescence, per unit area, may, for example, be less than 500%, 400%, 300%, 200%, 150%, or 100% of a gel autofluorescence of slab gel 54, per the same unit area and under the same irradiation with the ultraviolet light. Autofluorescence, as used herein, is background fluorescence produced by one or more substances other than the fluorophore(s) of interest. Any of the fluorescence or autofluorescence disclosed herein may include visible light and/or ultraviolet light, among others.

Figures 3, 4:
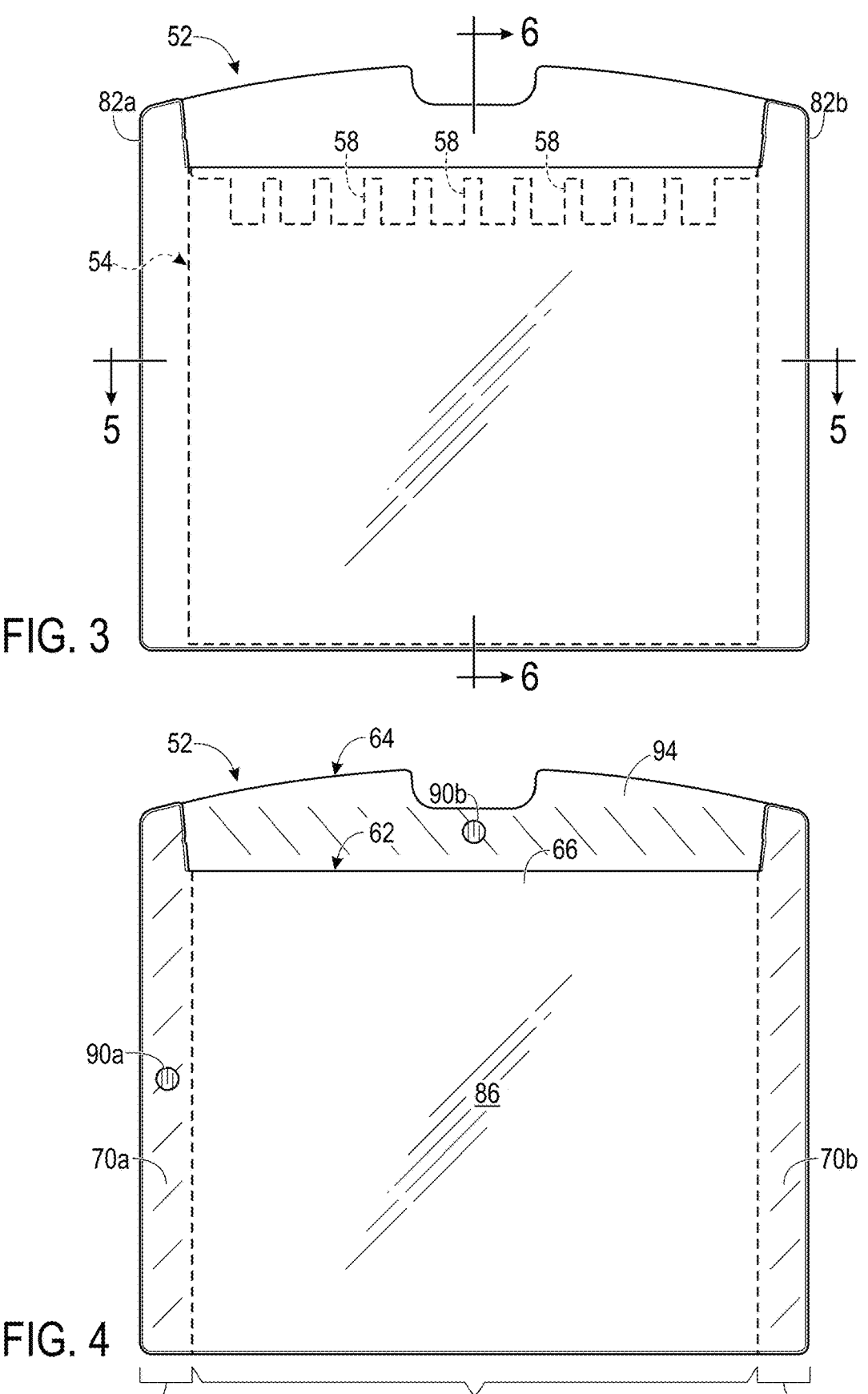
FIG. 3 is an orthogonal front view of the electrophoresis apparatus of FIG. 1, with the slab gel depicted in dashed outline.
FIG. 4 is another orthogonal front view of the electrophoresis apparatus of FIG. 1, taken in the absence of the slab gel and illustrating exemplary sites of polymer injection defined by discrete parts of the cassette.

Each plate 62, 64 may define a respective site of polymer injection 90a, 90b located outside viewing window 65 (see FIG. 4). The site of polymer injection for a molded part is the location at which polymer enters a mold in which the part is formed. The site of polymer injection may correspond to the position of a gate through which polymer enters the mold. If plates 62, 64 are formed by injection molding of a polymer into a pair of respective molds, such as at polymer injection sites 90a, 90b, the inventors have observed that each site of polymer injection 90a, 90b may be associated locally with an autofluorescence "scar" having an undesirably high level of UV-induced autofluorescence (also see Example 1). Accordingly, placing each polymer injection site outside viewing window 65, such as within one of the hatched regions of FIG. 4, prevents this undesirably high level of UV-induced autofluorescence from interfering with imaging slab gel 54 in situ. For example, in the depicted embodiment, front plate 62 defines site of polymer injection 90a in one of lateral edge regions 92a or 92b (i.e., in lateral edge portion 70a), and back plate 64 defines site of polymer injection 90b in upper edge portion 94 of back plate 64 above viewing window 65. In other embodiments, both plates 62, 64 may define respective sites of polymer injection each located in one of lateral edge regions 92a or 92b.

FIGS. 6 and 7 show sectional views of cassette 52 taken in the absence of slab gel 54. Front plate 62, back plate 64, and cavity 74 may have any suitable relative dimensions measured orthogonally to viewing window 65. For example, front plate 62 and back plate 64 may have respective thicknesses 96, 98 that are greater than, the same as, or less than a depth 100 of cavity 74. Smaller plate thicknesses 96, 98 may be used to reduce a thickness-dependent autofluorescence contribution of plates 62, 64, while still providing sufficient structural strength for cassette 54. A larger cavity depth 100 may be used to increase the sample-holding capacity of slab gel 54, thereby increasing the fluorescence of sample components relative to viewing window 65 of cassette 52.

The slab gel may be configured to resolve proteins of a sample by electrophoresis, such as polyacrylamide gel electrophoresis (PAGE). Accordingly, the slab gel may be an aqueous gel including any combination of a gel matrix (e.g., polyacrylamide, agarose, starch, etc.), an electrolyte, an amphipathic surfactant (e.g., sodium dodecyl sulfate (SDS)) to denature proteins and give each substantially the same charge per mass (for SDS-PAGE), a reducing agent (e.g., beta-mercaptoethanol), and a modifying agent, among others. Any suitable concentration of gel matrix may be used for the gel, such as 5-25% for a polyacrylamide gel, or 0.5% to 3% for an agarose gel. In some embodiments, the modifying agent may be configured to react with proteins driven into the gel by electrophoresis. The reaction may form fluorescent derivatives of the proteins, in response to irradiation of the viewing window with ultraviolet light. In some embodiments, the modifying agent may be a haloalkane, such as trichloroethanol, chloroform, trichloroacetic acid, trichloroethane, bromoform, or iodoacetic acid.

Apparatus 50 may be coupled to a tank assembly. The tank assembly may have an upper tank and a lower tank to hold respective electrolyte solutions. The upper end of apparatus 50 may be sealed to the upper tank, such as via a gasket, such that a respective electrode may be located in each of the tanks. Application of a voltage between the respective electrodes drives electrophoretic motion of charged components.

II. METHODS OF SAMPLE ANALYSIS

Figure 8:
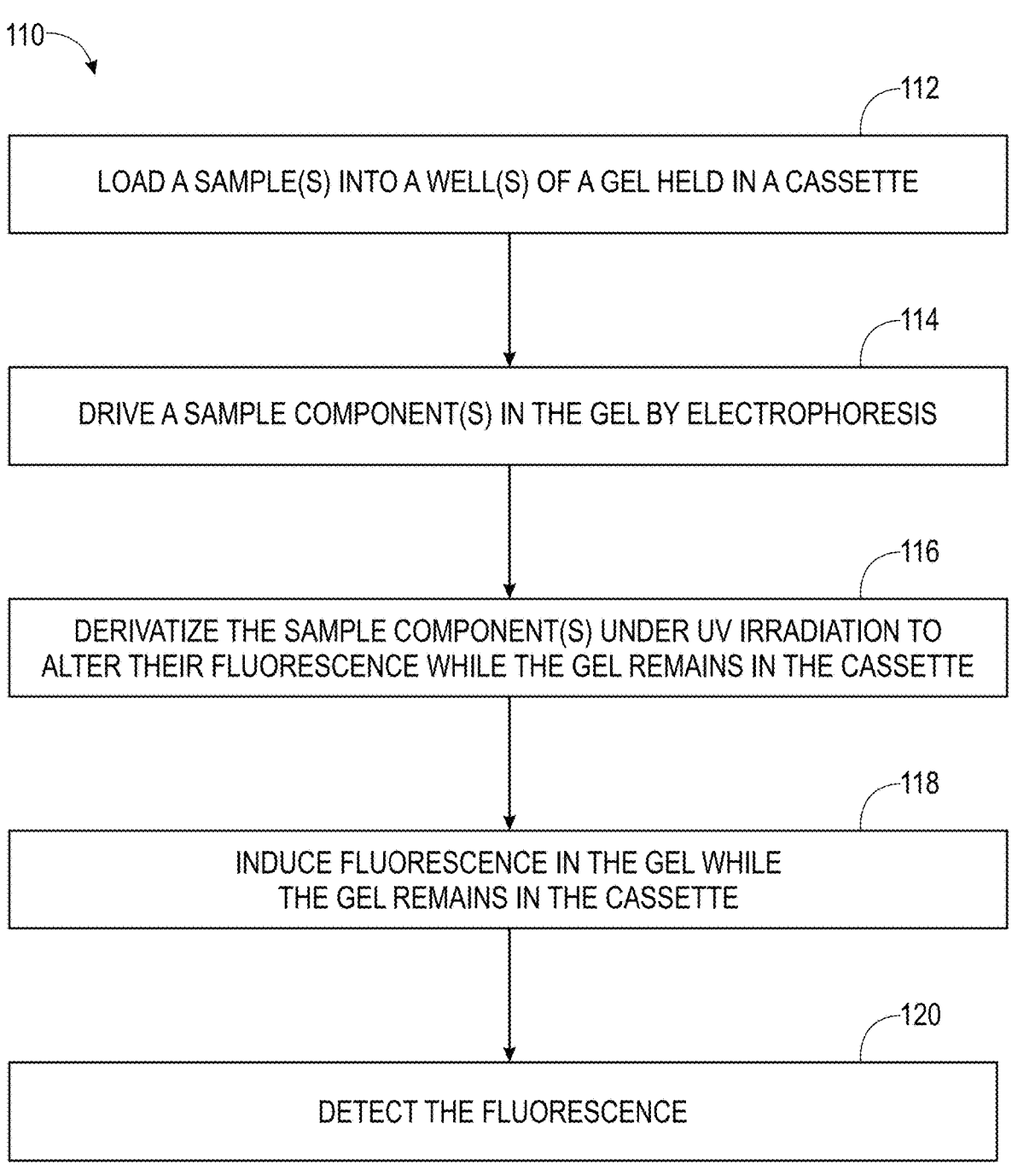
FIG. 8 is a flow diagram listing exemplary steps that may be performed, in any suitable order and combination, in a method of analyzing a sample using an electrophoresis apparatus in which gel processing is performed in situ.

This section describes exemplary methods of sample analysis using any of the electrophoretic apparatuses of the present disclosure (such as in Section I); see FIG. 8. The steps presented in a method 110 of sample analysis in FIG. 8 may be performed in any suitable order and combination.

One or more samples may be loaded into one or more wells of a gel held in a cassette, indicated at 112. The gel and cassette each may have any suitable combination of structures and features, for example, as described above in Section I. Loading samples may be performed before or after the electrophoresis apparatus has been coupled to a tank assembly (see Section I), and thus before or after the upper and lower edges of the gel have been placed into contact with respective electrolyte solutions (running buffer) held by corresponding tanks of the tank assembly. Each sample may include one or more sample components, such as one or more proteins.

One or more sample components of each sample may be driven in the gel by electrophoresis, indicated at 114. A voltage may be applied between a pair of electrodes located in respective tanks of a tank assembly, to create an electrophoretic potential between upper and lower edges of the gel. The electrophoretic potential may drive a sample component(s) of each sample from a corresponding well into the gel and along a lane extending from the well toward the lower edge of the gel. Each of the sample components may migrate at a velocity inversely related to the molecular weight of the sample component. Accordingly, electrophoresis may resolve sample components from one another according to size, with larger sample components traveling more slowly and being closer to the well when electrophoresis is terminated.

The sample component(s) in the gel may be derivatized under UV irradiation while the gel remains in the cassette, indicated at 116. In other words, UV-driven reaction of the modifying agent with sample components may be performed in situ, without opening the cassette. Derivatization of sample components with the modifying agent may be performed before, during, and/or after the electrophoresis of step 114. In some embodiments, the gel (and/or running buffer) may include the modifying agent. In some embodiments, the modifying agent may chemically react with the sample component(s), with the chemical reaction driven by ultraviolet light. This ultraviolet light may propagate to the gel through at least a portion of the cassette holding the gel, such as through at least one pane of the cassette's viewing window, to irradiate the gel and substances therein (e.g., proteins and a modifying agent) with ultraviolet light. The ultraviolet light may have any suitable wavelength, such as ultraviolet light of 320-400 nm (UV-A), 280-320 nm (UV-B), and/or <280 nm (UV-C), among others. This irradiation may be performed (i) after loading the sample into a well and before electrophoresis has started, (ii) while the sample component(s) is being electrophoresed in the gel, and/or (iii) after removal of the electrophoretic potential but while the gel is still located between panes of the viewing window. In some embodiments, the irradiation may promote formation of a fluorescent derivative of at least one protein of each sample. In some embodiments, the modifying agent that derivatizes the proteins may be a haloalkane, such as trichloroethanol, chloroform, trichloroacetic acid, trichloroethane, bromoform, or iodoacetic acid. In some embodiments, the modifying agent may chemically react with an amino acid residue, such as a tryptophan residue, present in the protein.

Fluorescence may be induced in the gel while the gel remains in the cassette, indicated at 118. In other words, derivatized, fluorescent sample components in the gel may be excited in situ, without opening the cassette. The fluorescence may be induced by irradiating the gel with ultraviolet light through at least one pane of a viewing window of the cassette to induce the fluorescence. The gel may be irradiated through the front pane, the back pane, or both the front and back panes of the viewing window. The ultraviolet light may have any suitable wavelength, such as ultraviolet light of 320-400 nm (UV-A), 280-320 nm (UV-B), and/or <280 nm (UV-C), among others. In some embodiments, ultraviolet light of the same wavelength may be used for steps 116 and 118 of method 110, such that steps 116 and 118 are performed in parallel.

Fluorescence induced in step 118 may be detected, indicated at 120. Detecting fluorescence may include capturing an image formed by the fluorescence. Detecting fluorescence alternatively or additionally may include monitoring fluorescence to determine when reaction of the modifying agent with sample components, such as proteins, has met a predefined condition, such as exceeding a threshold fluorescence. Monitoring fluorescence allows determining when the derivatization reaction and/or imaging is sufficiently complete to be stopped.

III. METHODS OF MAKING AN ELECTROPHORESIS APPARATUS

Figure 9:
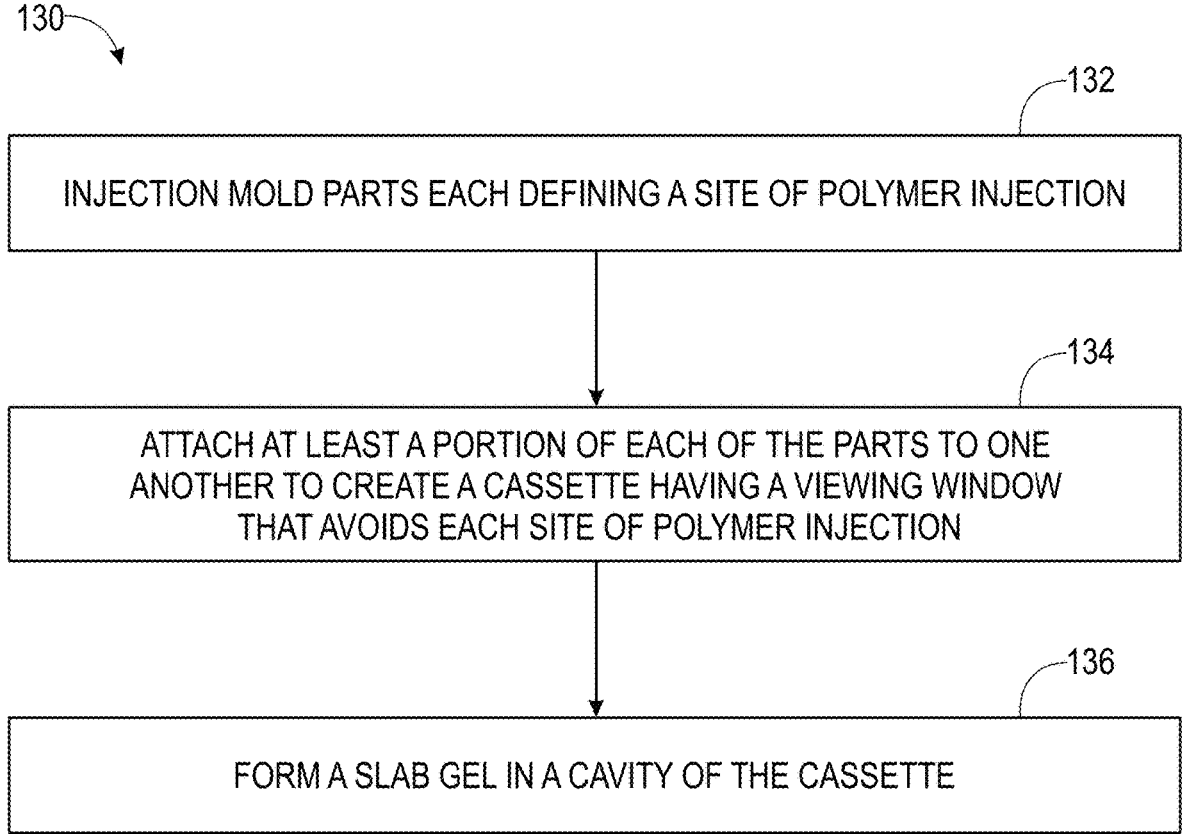
FIG. 9 is a flow diagram listing exemplary steps that may be performed, in any suitable order and combination, in a method of forming an electrophoresis apparatus having low UV-induced autofluorescence to enable gel processing in situ.

This section describes exemplary methods of making an electrophoresis apparatus having low autofluorescence to enable in situ processing of a gel contained by a cassette of the apparatus (such as in Section I); see FIG. 9. The steps presented in a method 130 of making an electrophoresis apparatus in FIG. 9 may be performed in any suitable order and combination.

A plurality of discrete parts may be injection molded, and each discrete part may define a site of polymer injection, indicated at 132. In some embodiments, a pair of plates may be injection molded. The pair of plates may be configured to provide panes of a viewing window. The site of polymer injection of each discrete part may be connected to, but spaced from, the corresponding pane when the discrete part is formed. In some embodiments, the site of polymer injection may be removed from the discrete part after the discrete part is formed, such as cut or broken off from the body of the discrete part, to at least partially form one of the plates.

The site of polymer injection may be locally autofluorescent relative to the rest of the corresponding part. The level of this local autofluorescence can be affected by molding parameters, such as heat and pressure. For example, heating the polymer longer and/or to a higher temperature may produce greater autofluorescence, as may placing the polymer under greater pressure and increased strain. Accordingly, to reduce or eliminate locally increased autofluorescence at the site of polymer injection, the polymer may be heated quickly, injected into the mold immediately, and then cooled quickly to minimize heating-related autofluorescence. Alternatively, or in addition, the polymer may be injected at a slower rate, under less pressure, to minimize pressure/strain-related autofluorescence.

The parts may be attached to one another to create a cassette having a viewing window that avoids each polymer injection site of the plurality of discrete parts, indicated at

134. The viewing window may include a front pane and a back pane having a cavity located between them.

A slab gel may be formed in the cavity of the cassette, indicated at 136. The slab gel may be formed by gelation using a polymer (e.g., agarose) or a polymer precursor (such as acrylamide). Because the viewing window avoids each site of polymer injection, the slab gel may be imaged after electrophoresis and labeling, without imaging any locally autofluorescent sites of polymer injection of the cassette.

IV. EXAMPLES

The section describes further aspects of the electrophoresis apparatuses of the present disclosure. These aspects are presented here for illustration and are not intended to limit the scope of the present disclosure.

Example 1. Electrophoresis Apparatuses Composed of Different Polymers

Figures 10, 11:
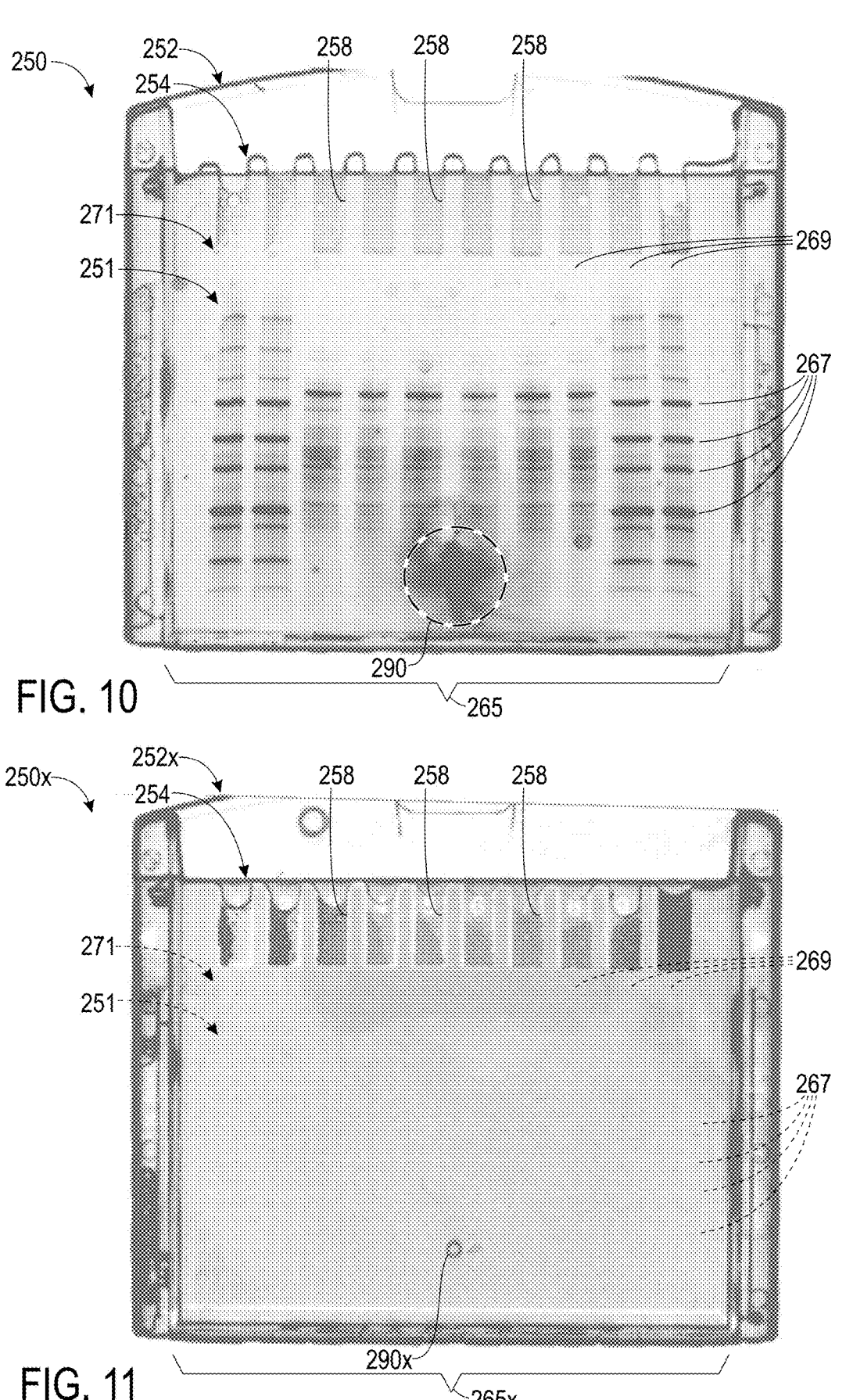
FIG. 10 is a fluorescence image of an exemplary electrophoresis apparatus including a cassette and a slab gel, taken after electrophoresis of proteins in lanes of the slab gel and derivatization of the proteins under UV irradiation to render them fluorescent with a peak of emission in the visible spectrum, wherein the cassette defines a viewing window that is UV transparent and minimally autofluorescent to enable gel processing in situ.
FIG. 11 is a fluorescence image for comparison FIG. 10, which was generated generally as in FIG. 10 except using a cassette defining a viewing window that is not transparent to ultraviolet light, such that bands of fluorescent derivatized proteins are not visible.

This example shows images of two embodiments 250, 250x of electrophoresis apparatus 50 taken after gel electrophoresis and in situ derivatization of samples 251 in a slab gel 254 of each apparatus 250, 250x; see FIGS. 10 and 11 (also see FIGS. 1-7).

Electrophoresis apparatuses 250, 250x include respective cassettes 252, 252x for slab gel 254. Cassette 252 provides a viewing window 265 suitable for in situ derivatization and imaging of slab gel 254 (see FIG. 10). Cassette 252 (and thus viewing window 265) is formed of a polyacrylate polymer (Poly(methyl methacrylate)—PMMA) that is UV transparent and has low UV-inducible autofluorescence. More specifically, cassette 252 is composed of CA-41 UVT-LL2 polymer, which is commercially available from Plaskolite (Columbus, Ohio, USA). In contrast, cassette 252x provides a viewing window 265x that does not permit in situ derivatization and imaging (see FIG. 11). Cassette 252x (and thus viewing window 265x) is composed of a copolymer of styrene and acrylonitrile (SAN polymer) that is not UV transparent.

Protein-containing samples 251 were loaded into wells 258 of each slab gel 254. Proteins 267 of samples 251 were electrophoresed in lanes 269 of a resolving portion 271 of each slab gel 254 by application of an electrophoretic potential. Each viewing window 265, 265x was then irradiated with ultraviolet light to encourage derivatization of proteins 267 in situ in slab gel 254 by chemical reaction with a haloalkane modifying agent (2,2,2-trichloroethanol) present in the slab gel (i.e., incorporated into the slab gel when formed). The haloalkane modifying agent reacts with tryptophan residues of proteins 267 to alter their fluorescence for emission in the visible spectrum.

The specific polymer forming viewing window 265 or 265x determines whether proteins 267 in each slab gel are detectable in the captured images. To drive derivatization of proteins 267 in situ, the polymer needs to be transparent to UV, to permit efficient UV irradiation of slab gel 254 through at least one pane of cassette 252 or 252x. Accordingly, viewing window 265x, which is not transparent to ultraviolet light, does not permit sufficient derivatization of proteins 267 with the haloalkane label. Moreover, even if proteins 267 were derivatized inside viewing window 265x, viewing window 265x also would not permit excitation of the derivatized proteins with ultraviolet light. Furthermore, to detect fluorescence from in situ derivatized proteins 267, which may generate a relatively weak fluorescence signal, the autofluorescence of slab gel 254 and viewing window 265 must be low, to create a sufficient signal to noise ratio in the captured images. The polyacrylate used to form viewing window 265 is both UV transparent and only minimally autofluorescent, which permits derivatized proteins 267 to be detectable readily over background.

Respective sites of polymer injection 290, 290x are also marked in the images of FIGS. 10 and 11. Site of polymer injection 290 of viewing window 265 produces a strong, localized fluorescence signal in FIG. 10, because viewing window 265 is UV transparent and only minimally autofluorescent. Moving site of polymer injection 290 to a position outside viewing window 265, as described above in Section I, advantageously prevents the fluorescence of the site of polymer injection 290 from overlapping proteins 267 in the captured image. Site of polymer injection 290x of viewing window 265x is barely visible in FIG. 11 because viewing window 265x is not transparent to ultraviolet light.

Example 2. Comparison of Polyacrylates

Figures 12, 13:
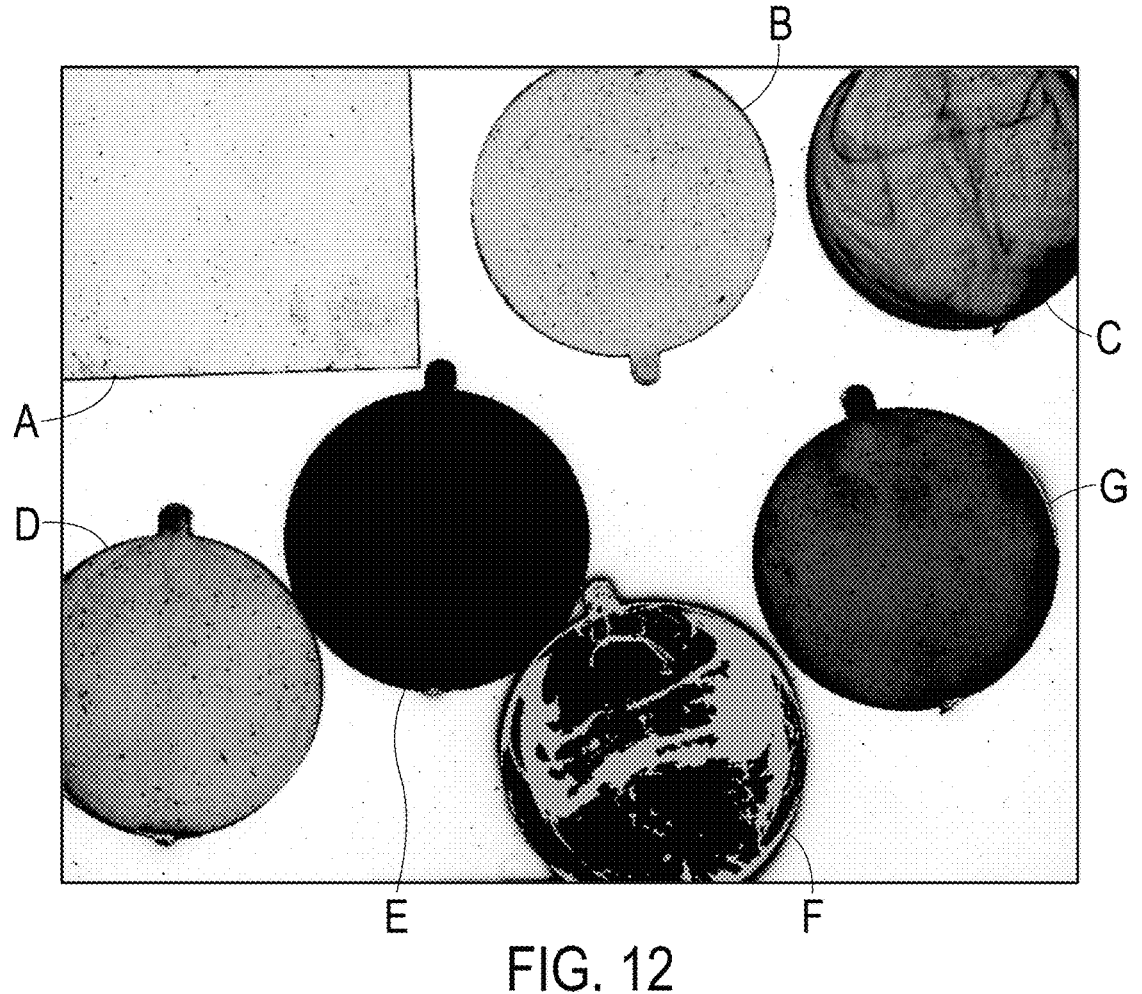
FIG. 12 is a fluorescence image of seven different acrylate specimens (A-G) taken under UV irradiation to induce autofluorescence.
FIG. 13 is a table listing the relative levels of autofluorescence of the seven different acrylate specimens of FIG. 12.

This example describes a comparison of the autofluorescence detected from a set of seven polyacrylate formulations that are commercially available from Plaskolite (Columbus, Ohio, USA); see FIGS. 12 and 13.

FIG. 12 shows a fluorescence image of seven different acrylate specimens (A-G) taken under UV irradiation to induce autofluorescence. Each of the specimens is substantially transparent to the ultraviolet light used for UV irradiation, but the specimens vary widely in their ability to autofluoresce in response to the UV irradiation. Strong autofluorescence makes specimens darker in the image (compare with the background between the specimens.)

FIG. 13 shows a table listing the relative levels of autofluorescence of the seven different polyacrylate specimens of FIG. 12. Specimen A (Utran®) has the lowest autofluorescence, while Specimen F (CA-83 UVT (N)) has the highest autofluorescence, over 75-fold higher than Specimen A. Identifying and using a polymer that is both UV transparent and only minimally autofluorescent is critical for derivatization and imaging proteins in a slab gel through a pane(s) of a viewing window of a cassette holding the slab gel.

V. SELECTED ASPECTS 1

This section describes selected aspects of the electrophoresis apparatuses and methods of the present disclosure as a series of indexed paragraphs.

Paragraph A1. An electrophoresis apparatus for sample analysis, comprising: (i) a cassette defining a cavity between a first pane and a second pane of a viewing window; and (ii) a slab gel located in the cavity; wherein the viewing window is transparent to ultraviolet light, wherein the viewing window, absent the slab gel, defines a window autofluorescence inducible by irradiation with the ultraviolet light, and wherein the window autofluorescence, per unit area, is less than five-fold a gel autofluorescence of the slab gel, per the same unit area and under the same irradiation with the ultraviolet light.

Paragraph A2. The electrophoresis apparatus of paragraph A1, wherein the cassette includes a first plate including the first pane and a second plate including the second pane, and wherein each plate is (a) an injection-molded part defining a site of polymer injection that is spaced from the viewing window in the cassette or (b) formed from an injection-molded part at least partially by physically removing a site of polymer injection from such injection-molded part.

Paragraph A3. The electrophoresis apparatus of paragraph A2, wherein the cassette has an autofluorescence that increases locally around at least one site of polymer injection.

Paragraph A4. The electrophoresis apparatus of paragraph A2 or A3, wherein at least one of the first and second plates defines a site of polymer injection formed by a lateral edge portion of the cassette or by a top or bottom portion of the first plate or the second plate that does not overlap the other plate in the cassette.

Paragraph A5. The electrophoresis apparatus of any of paragraphs A1 to A4, wherein the slab gel defines a plurality of wells and includes a resolving portion having a plurality of lanes aligned with the plurality of wells, and wherein the resolving portion is contained in the viewing window.

Paragraph A6. The electrophoresis apparatus of any of paragraphs A1 to A5, wherein the slab gel is configured to resolve proteins of a sample by electrophoresis, and wherein the slab gel includes a modifying agent configured to derivatize proteins to alter a fluorescence thereof.

Paragraph A7. The electrophoresis apparatus of paragraph A6, wherein the modifying agent is configured to derivatize proteins in the gel, in response to irradiation of the viewing window with ultraviolet light.

Paragraph A8. The electrophoresis apparatus of paragraph A7, wherein the modifying agent is a haloalkane selected from the group consisting of trichloroethanol, chloroform, trichloroacetic acid, trichloroethane, bromoform, and iodoacetic acid.

Paragraph A9. The electrophoresis apparatus of any of paragraphs A1 to A8, wherein the window autofluorescence is less than the gel autofluorescence.

Paragraph A10. The electrophoresis apparatus of any of paragraphs A1 to A9, wherein the cassette is formed of polyacrylate.

Paragraph A11. The electrophoresis apparatus of any of paragraphs A1 to A10, wherein the window autofluorescence is less than four-fold, three-fold, or twice the gel autofluorescence, or is less than the gel autofluorescence.

Paragraph B1. A method of analyzing a sample, the method comprising: (i) electrophoresing one or more proteins of the sample in a slab gel held in a cassette, the cassette including a first plate, a second plate, and a viewing window that is transparent to ultraviolet light and extends through the cassette from an outer surface of the first plate, through the slab gel, to an outer surface of the second plate; (ii) irradiating at least a portion of the viewing window of the cassette with ultraviolet light while the slab gel is held in the cassette; and (iii) detecting fluorescence of the one or more proteins, or derivatives thereof, the fluorescence being induced by irradiating and being detected after propagation through at least one of the first and second plates of the viewing window; wherein the viewing window, absent the slab gel, has a window autofluorescence per unit area, in response to irradiating, that is less than five-fold a background fluorescence of the slab gel.

Paragraph B2. The method of paragraph B1, wherein irradiating drives chemical reaction of a modifying agent in the gel with the one or more proteins of the sample to form the derivatives of the one or more proteins, and wherein detecting fluorescence includes detecting fluorescence emitted by the derivatives.

Paragraph B3. The method of paragraph B2, wherein the modifying agent is a haloalkane selected from the group consisting of trichloroethanol, chloroform, trichloroacetic acid, trichloroethane, bromoform, and iodoacetic acid.

Paragraph B4. The method of any of paragraphs B1 to B3, wherein detecting fluorescence includes capturing one or more images formed by the fluorescence.

Paragraph B5. The method of paragraph B4, wherein capturing is stopped when the fluorescence detected has met one or more predefined criteria.

Paragraph B6. The method of any of paragraphs B2 to B5, wherein detecting fluorescence includes monitoring fluorescence to determine when the reaction of the modifying agent has met a predefined condition, and wherein, optionally, irradiating is stopped when the predefined condition has been met.

Paragraph B7. The method of any of paragraphs B1 to B6, wherein each plate is (a) an injection-molded part defining a site of polymer injection that is spaced from the viewing window or (b) formed from an injection-molded part at least partially by physically removing a site of polymer injection from such injection-molded part.

Paragraph B8. The method of any of paragraphs B1 to B7, wherein the window autofluorescence is less than four-fold, three-fold, or twice the background autofluorescence, or is less than the background autofluorescence.

Paragraph C1. A method of forming an electrophoresis apparatus for sample analysis, the method comprising: (i) injection molding two or more discrete parts, wherein each discrete part defines a site of polymer injection; (ii) attaching at least a portion of each of the two or more discrete parts to one another to create a cassette, the cassette defining a cavity between a first pane and a second pane of a double-paned viewing window, wherein each site of polymer injection is (a) included in the cassette and avoids the viewing window or (b) absent from the cassette; and (iii) forming a slab gel in the cavity; wherein the viewing window is transparent to ultraviolet light, wherein the viewing window, absent the slab gel, has a window autofluorescence inducible by irradiation with the ultraviolet light, and wherein the window fluorescence, per unit area, is less than five-fold a gel autofluorescence of the slab cell, per the same unit area and under the same irradiation with the ultraviolet light.

Paragraph C2. The method of paragraph C1, wherein the cassette has an autofluorescence that increases locally around each site of polymer injection.

Paragraph C3. The method of paragraph C1 or C2, wherein the first pane is formed by a first plate, wherein the second pane is formed by a second plate, wherein at least one of the first and second plates defines a site of polymer injection formed by a lateral edge region of the cassette or by a top or bottom portion of the first plate or the second plate that does not overlap the other plate.

Paragraph C4. The method of any of paragraphs C1 to C3, wherein the first pane is provided by a plate, further comprising physically removing the site of polymer injection from one of the discrete parts to at least partially form the first plate, wherein, optionally, removing includes cutting or breaking the one discrete part to remove the site of polymer injection.

Paragraph C5. The method of any of paragraphs C1 to C3, wherein attaching includes bonding a pair of the two or more discrete parts to one another.

Paragraph C6. The method of any of paragraphs C1 to C5, wherein the window autofluorescence is less than four-fold, three-fold, or twice the gel autofluorescence, or is less than the gel autofluorescence.

The term "exemplary" as used in the present disclosure means "illustrative" or "serving as an example" and does not imply desirability or superiority.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. An electrophoresis apparatus for sample analysis, comprising:
a cassette defining a cavity between a first pane and a second pane of a viewing window, wherein the cassette includes a first plate including the first pane and a second plate including the second pane, and wherein each plate is an injection-molded part having an autofluorescent scar corresponding to a site of polymer injection that is spaced from the viewing window;
a slab gel located in the cavity;
wherein the viewing window is transparent to ultraviolet light, wherein the viewing window, absent the slab gel, defines a window autofluorescence inducible by irradiation with the ultraviolet light, and wherein the window autofluorescence, per unit area, is less than five-fold a gel autofluorescence of the slab gel, per the same unit area and under the same irradiation with the ultraviolet light.

2. The electrophoresis apparatus of claim 1, wherein the cassette has an autofluorescence that increases locally around the site of polymer injection of each plate.

3. The electrophoresis apparatus of claim 1, wherein the site of polymer injection of each plate is formed by a lateral edge portion of the cassette.

4. The electrophoresis apparatus of claim 1, wherein the slab gel defines a plurality of wells and includes a resolving portion having a plurality of lanes aligned with the plurality of wells, and wherein the resolving portion is contained in the viewing window.

5. The electrophoresis apparatus of claim 1, wherein the slab gel is configured to resolve proteins of a sample by electrophoresis, and wherein the slab gel includes a modifying agent configured to derivatize the proteins to alter a fluorescence thereof.

6. The electrophoresis apparatus of claim 5, wherein the modifying agent is configured to derivatize the proteins in the slab gel, in response to irradiation of the viewing window with the ultraviolet light.

7. The electrophoresis apparatus of claim 6, wherein the modifying agent is a haloalkane selected from the group consisting of trichloroethanol, chloroform, trichloroacetic acid, trichloroethane, bromoform, and iodoacetic acid.

8. The electrophoresis apparatus of claim 1, wherein the window autofluorescence is less than the gel autofluorescence.

9. The electrophoresis apparatus of claim 1, wherein the cassette is formed of polyacrylate.

10. The electrophoresis apparatus of claim 1, wherein each autofluorescent scar is on a lateral edge region or on a top or bottom portion of each plate that does not overlap the other plate.

* * * * *